United States Patent
Godwin

(10) Patent No.: US 11,946,099 B2
(45) Date of Patent: Apr. 2, 2024

(54) ELIMINATION OF PRIMER-PRIMER INTERACTIONS DURING PRIMER EXTENSION

(71) Applicant: Roche Sequencing Solutions, Inc., Pleasanton, CA (US)

(72) Inventor: Brian Godwin, Livermore, CA (US)

(73) Assignee: ROCHE SEQUENCING SOLUTIONS, INC., Pleasanton, CA (US)

( * ) Notice: Subject to any disclaimer, the term of this patent is extended or adjusted under 35 U.S.C. 154(b) by 305 days.

(21) Appl. No.: 17/183,255

(22) Filed: Feb. 23, 2021

(65) Prior Publication Data

US 2021/0254146 A1 Aug. 19, 2021

Related U.S. Application Data

(63) Continuation of application No. 16/080,151, filed as application No. PCT/EP2017/053922 on Feb. 21, 2017, now Pat. No. 10,961,567.

(60) Provisional application No. 62/299,988, filed on Feb. 25, 2016.

(51) Int. Cl.
| | |
|---|---|
| *C12Q 1/6848* | (2018.01) |
| *C12Q 1/6806* | (2018.01) |
| *C12Q 1/6809* | (2018.01) |
| *C12Q 1/6811* | (2018.01) |
| *C12Q 1/6855* | (2018.01) |
| *C12Q 1/686* | (2018.01) |

(52) U.S. Cl.
CPC ......... *C12Q 1/6848* (2013.01); *C12Q 1/6806* (2013.01); *C12Q 1/6809* (2013.01); *C12Q 1/6811* (2013.01); *C12Q 1/6855* (2013.01); *C12Q 1/686* (2013.01); *C12Q 2525/101* (2013.01); *C12Q 2525/186* (2013.01)

(58) Field of Classification Search
None
See application file for complete search history.

(56) References Cited

U.S. PATENT DOCUMENTS

2012/0065091 A1* 3/2012 Willis ............... C12Q 1/6858
506/9

\* cited by examiner

*Primary Examiner* — Samuel C Woolwine
(74) *Attorney, Agent, or Firm* — Eric Grant Lee

(57) ABSTRACT

The invention comprises a method of amplifying nucleic acids by primer extension with reduced formation of primer-primer byproducts.

10 Claims, 5 Drawing Sheets

MIP hybridized to the
target nucleic acid

MIP hybridized to a second MIP
Priming is initiated

Polymerase extension proceeds
Ligation closes circle
Product is portected from exonucleases
Universal primer amplification
produces off target result MIP hybridized to a second MIP
Priming is initiated Polymerase extension stops
Ligation is not possible
MIPs will be digested by exonucleases
No product is amplified by universal
primer PCR

ELIMINATION OF PRIMER-PRIMER INTERACTIONS DURING PRIMER EXTENSION

FIELD OF THE INVENTION

The invention relates generally to in vitro analysis of nucleic acid targets and more particularly, to improved method of enrichment of nucleic acid targets by primer extension.

BACKGROUND OF THE INVENTION

Primer dimers and other primer-primer interactions are undesirable artifacts of in vitro nucleic acid synthesis reactions. Primer design tools are commonly used to avoid primer sequences capable of cross-hybridization or self-hybridization. However, studies have shown that little or no complementarity is required for primer dimers to form and become extended or replicated. Brownie, J., et al. (1997) *The elimination of primer dimers during PCR*, Nucl. Acids Res., 25:3235. The suggested explanation is that high concentration of primers and low concentration of the target sequence create thermodynamically favorable conditions for primer-primer annealing and extension.

Primer dimers can lead to undesirable side products that consume reagents and compete with amplification of true targets. There is therefore a need for a method of eliminating or reducing primer-primer interactions. Such a method will especially benefit applications where rare nucleic acid targets are to be detected. Such a method will especially benefit clinical diagnostics and the newly emerging field of liquid biopsy, or detection of multiple rare nucleic targets in human plasma.

SUMMARY OF THE INVENTION

In some embodiments, the invention is a method of synthesizing nucleic acid strands by primer extension with reduced primer-primer interaction comprising: contacting a target nucleic strand with a nucleic acid polymerase and a primer comprising at least one modified nucleotide that stalls nucleotide incorporation by the polymerase. The primer can be a single-stranded oligonucleotide consisting of two arms complementary to a target sequence separated by a linker sequence non-complementary to the target sequence. The polymerase can be an archaeal B-family polymerase or a replicative polymerase. The modified nucleotide can be uracil, an abasic nucleotide or a pyrimidine dimer.

In another embodiment, the invention is a method of amplifying a target nucleic acid in a sample with reduced primer-primer interaction comprising: a primer extension step, wherein the sample is contacted with a nucleic acid polymerase and a first primer complementary to the target nucleic acid comprising at least one modified nucleotide that stalls nucleotide incorporation by the polymerase, to generate a primer extension product; and an exponential amplification step wherein the sample is contacted with a second primer complementary to the primer extension product. The primer extension product may be ligated to a double stranded adaptor prior to the amplification step. The adaptor and the first primer may comprise binding sites for universal amplification primers and the second primer may be a universal primer. The primer may be a single-stranded oligonucleotide consisting of two arms complementary to a target sequence separated by a linker sequence non-complementary to the target sequence. The exponential amplification step may utilize a polymerase tolerant of the modified nucleotide. In some embodiments, the method further comprises a purification step before the amplification step, wherein the first primer and the template nucleic acid are separated from the primer extension product. In some embodiments, the modified nucleotide is uracil. The method may comprise a carryover prevention step prior to the amplification step, wherein the sample is contacted with Uracil DNA glycosylase.

In another embodiment, the invention is a kit for synthesizing nucleic acid strands by primer extension with reduced primer dimer formation comprising a nucleic acid polymerase and a first primer complementary to the first strand of the target nucleic acid and comprising at least one modified nucleotide that stalls nucleotide incorporation by the polymerase. The kit may further comprise a second primer complementary to the second strand of the target nucleic acid or an adaptor. The primer may be a single-stranded oligonucleotide consisting of two arms complementary to a target sequence separated by a linker sequence non-complementary to the target sequence.

In yet another embodiment, the invention is a reaction mixture for synthesizing nucleic acid strands by primer extension with reduced primer dimer formation comprising a nucleic acid polymerase and a first primer complementary to the first strand of the target nucleic acid and comprising at least one modified nucleotide that stalls nucleotide incorporation by the polymerase.

DETAILED DESCRIPTION OF THE INVENTION

Definitions

Figure 1:
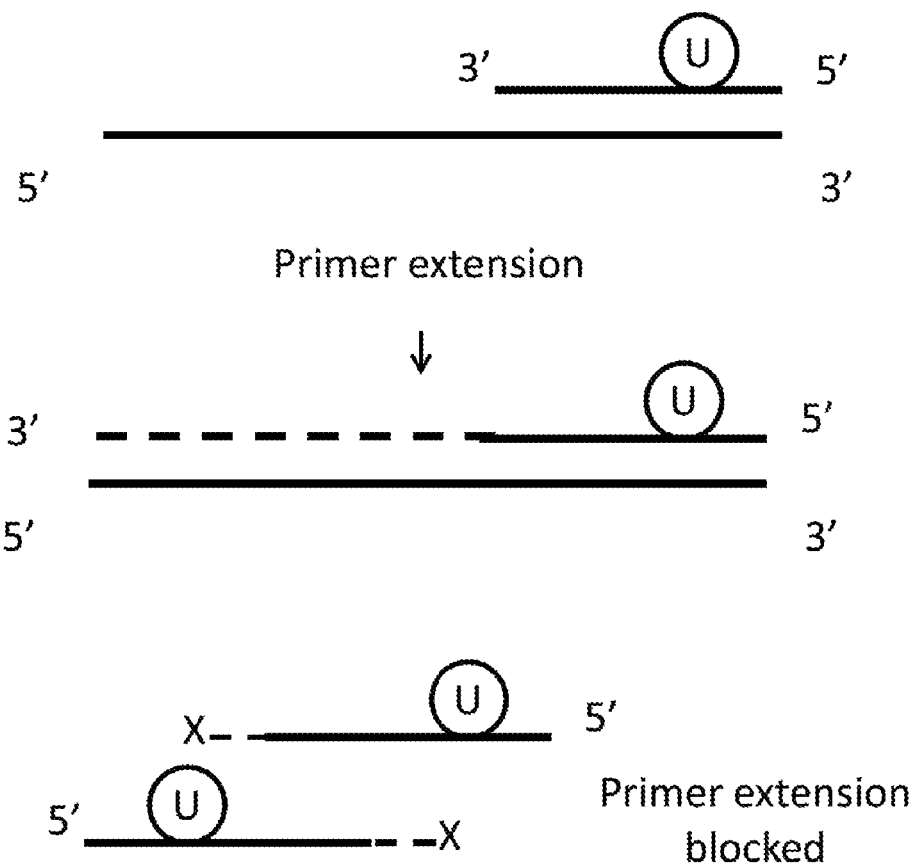
FIG. 1 is a diagram of the method of the invention showing a non-extendable primer dimer artifact.

The term "polymerase" refers to a nucleic acid polymerase, whether native (purified from its native species) or recombinant (produced in and purified from a transformed host). In the context of the invention, the polymerase may have its original amino acid sequence or a modified amino acid sequence as long as the polymerase maintains its ability to stall replication at the modified base according to the method of the invention.

The terms "stall" and "stall replication" refer to slowing the rate or complete cessation of nucleotide incorporation by the polymerase. The stalled polymerase may remain bound to the substrate or dissociate from the substrate.

The term "modified nucleotide" refer to a deoxyribonucleotide or ribonucleotide containing a base other than adenosine, guanosine, thymidine or cytosine. The modified nucleotide can be abasic (have no base). The modified base can contain a modification found in nature: deamination, methylation, oxidation or a UV-induced linkage. The modified base can contain a modification not found in nature.

The term "probe" means any molecule that is capable of selectively binding to a specifically intended target biomolecule, for example, a nucleic acid sequence of interest to be bound, captured or hybridized by the probes.

The term "adaptor" means a nucleotide sequence that may be added to another sequence so as to import additional properties to that sequence. An adaptor can be single- or double-stranded, or may have both a single-stranded portion and a double-stranded portion.

The term "universal primer" and "universal priming site" refer to a primer and priming site not naturally present in the target sequence. Typically, the universal priming site is present in adaptors or target-specific primers. The universal primer can bind to and direct primer extension from the universal priming site.

The term "primer dimer" refers to a product of annealing of two oligonucleotide primers present in the same reaction vessel. The primer dimer may be formed by two identical primers or two primers with different sequences. The primer dimer may involve one or more regions of base pairing between the two primers. The base pairing may be Watson-Crick base pairing as well as additional hydrogen bonding (e.g., Hoogsteen pairing, or base stacking) that stabilizes a double-stranded nucleic acid. The primer dimer may comprise annealed primers or annealed and extended primers.

The term "replicative polymerase" refers to chromosomal replicases sharing the common properties and structures. The common properties include the ability to processively extend a nucleic acid primer utilizing a single-stranded DNA template (no de novo synthesis). The common structures include the palm, fingers and thumb domains, see Johansson et al., (2013) *Replicative DNA Polymerases*, Cold Spring Harb Perspect Biol. 5(6):a012799. Replicative polymerases include human and yeast Polymerase epsilon and Polymerase delta, archaeal Pol B and eubacterial Pol III.

The present invention provides a method of synthesizing nucleic acid strands by primer extension with reduced primer-primer interaction comprising: contacting a target nucleic strand with a nucleic acid polymerase and a primer comprising at least one modified nucleotide that stalls nucleotide incorporation by the polymerase. The primer may be a single-stranded oligonucleotide consisting of two arms complementary to a target sequence separated by a linker sequence non-complementary to the target sequence. The polymerase may be an archaeal B-family polymerase or a replicative polymerase. The modified nucleotide may for example be be uracil, an abasic modified nucleotide or a pyrimidine dimer.

The present invention also provides method of amplifying a target nucleic acid in a sample with reduced primer-primer interaction comprising a) a primer extension step, wherein the sample is contacted with a nucleic acid polymerase and a first primer complementary to the target nucleic acid comprising at least one modified nucleotide that stalls nucleotide incorporation by the polymerase, to generate a primer extension product; and b) an exponential amplification step wherein the sample is contacted with a second primer complementary to the primer extension product. The primer extension product may be ligated to a double stranded adaptor prior to step b). The adaptor and the first primer may comprise binding sites for universal amplification primers and the second primer is a universal primer. The primer may be a single-stranded oligonucleotide consisting of two arms complementary to a target sequence separated by a linker sequence non-complementary to the target sequence. The exponential amplification step may utilize a polymerase tolerant of the modified nucleotide. Prior to step b), a purification may be performed. The modified nucleotide may be uracil. In this step, the method may further comprise a carryover prevention step prior to step b), wherein the sample is contacted with Uracil DNA glycosylase.

The present invention also provides a kit for synthesizing nucleic acid strands by primer extension with reduced primer dimer formation comprising a nucleic acid polymerase and a first primer complementary to the first strand of the target nucleic acid and comprising at least one modified nucleotide that stalls nucleotide incorporation by the polymerase. Said kit may further comprise a second primer complementary to the second strand of the target nucleic acid, and/or an adaptor. The primer may be a single-stranded oligonucleotide consisting of two arms complementary to a target sequence separated by a linker sequence non-complementary to the target sequence.

The present invention in addition provides a reaction mixture for synthesizing nucleic acid strands by primer extension with reduced primer dimer formation comprising a nucleic acid polymerase and a first primer complementary to the first strand of the target nucleic acid and comprising at least one modified nucleotide that stalls nucleotide incorporation by the polymerase.

The present invention comprises a method of reducing and eliminating primer-primer interactions occurring during in vitro nucleic acid synthesis reactions where oligonucleotide primers are present. Such primer-primer interactions are often due to partial complementarity and weak base pairing between oligonucleotide primers. Empirical primer design methods and software tools exist to minimize or avoid such base pairing. However, these methods have limited applicability to multiplex reactions. Where dozens of even hundreds of different oligonucleotide primers are present, some cross-complementarity is difficult if not impossible to avoid. During highly multiplexed primer extension or exponential amplification reactions, primer-primer interactions can lead to undesirable side products commonly referred to as primer dimers. The major contributor to these side products is polymerase extension of a primer using a separate primer as a template. While cross-complementarity and primer-primer annealing is difficult to prevent, reducing or eliminating extension of annealed primer pairs would diminish or eliminate formation of the undesirable side products.

In one embodiment, the invention is a method of amplifying nucleic acid targets with reduced or eliminated primer dimer formation. The method comprises contacting a sample containing one or more target nucleic acids with a nucleic acid polymerase and one or more extension primers containing modified bases that cause stalling of the nucleic acid polymerase during primer extension. The nucleic acid polymerase will stall during extension of a primer within a primer dimer where the modified nucleotide is present in its path. The target nucleic acid is not expected to contain the modified nucleotide and the polymerase will not stall during extension of a primer annealed to the target nucleic acid. (FIG. 1) Certain polymerases stall replication when they encounter unusual nucleotides in the template strand that may reflect DNA damage sites. For example, uracil in DNA causes several polymerases to stall, including several archaeal B-family and D-family polymerases, e.g., Pfu polymerase. See Wardle, et al., (2007) *Uracil recognition by replicative DNA polymerases is limited to the archaea, not* occurring with bacteria and eukarya, Nucl. Acids Res., 36:705. Abasic sites cause the prokaryotic and eukaryotic replicative enzymes to stall, e.g., Pol III of *E. coli* and Polymerase delta of yeast. See Goodman, M. (2000) *Coping with replication 'train wrecks' in Escherichia coli using Pol V, Pol II and RecA proteins*. Trends in Biochem. Sci., 25:189; and Boiteux, et al., (2004) *Abasic sites in DNA: repair and biological consequences in Saccharomyces cerevisiae*, DNA Repair 3:1. Cyclobutane pyrimidine dimers and (6-4) photoproducts (TT dimers) caused by UV light irradiation are also known to stall archaeal and eukaryotic (including mammalian) replicative polymerases. Ghosal et al., (2013) *DNA damage tolerance: a double-edged sword guarding the genome*, Transl. Cancer Res. 2:107; Jozwiakowski, et al., (2015) *Archaeal replicative primases can perform translesion DNA synthesis PNAS* 112 (7) E633-E638. The pyrimidine dimers along with modified bases may be incorporated into an oligonucleotide primer via the phorphoramidite method. Yamamoto, et al. (2006) *Chemical synthesis of oligodeoxy-ribonucleotides containing the Dewar valence isomer of the* (6-4) *photoproduct and their use in* (6-4) *photolyase studies*, Nucl. Acids Res. 34:4406. In addition to the specific examples described herein, the description of the invention enables use of any other modified nucleotide (either known or yet to be synthesized) that can be incorporated into a primer and is capable of stalling the DNA polymerase.

In some embodiments, the method comprises contacting the sample with an extension primer containing one or more uracils, or one or more abasic sites, or one or more pyrimidine dimers and an archaeal B-family DNA polymerase (e.g., Pfu polymerase). In other embodiments, the method comprises contacting the sample with an extension primer containing one or more pyrimidine dimers or abasic sites and a eukaryotic or archaeal replicative DNA polymerase or a derivative thereof.

In some embodiments, the primer incorporating the modified nucleotide is a short oligonucleotide mostly consisting of a single region of partial or exact complementarity with the target nucleic acid (FIG. 1). In addition to the region of complementarity to the target, the primer may optionally comprise additional sequences for downstream steps such as restriction site or a sequence complementary to a universal amplification primer binding site, a universal sequencing primer binding site or a barcode.

Figure 2:
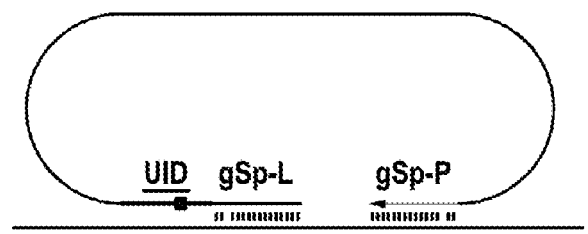
FIG. 2 is a diagram showing formation of the artifact formed by hybridized and extended molecular inversion probes (MIP).
Figure 2:
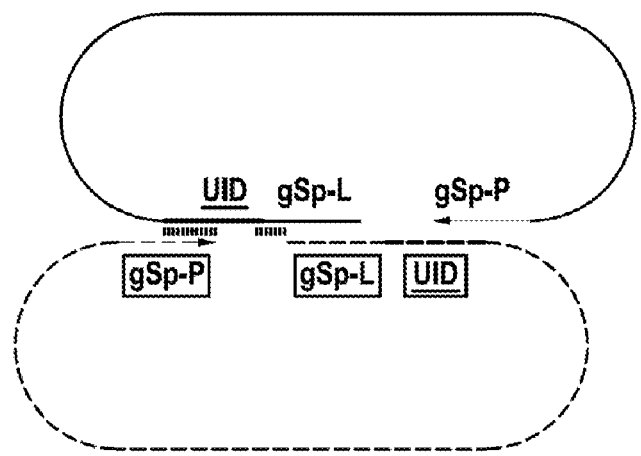
Figure 2:
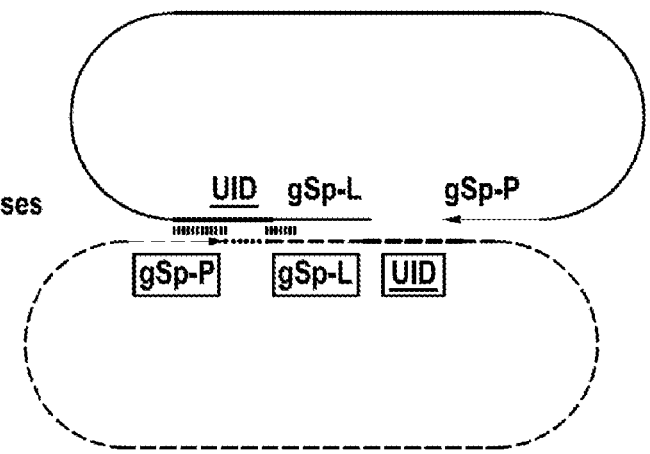

In other embodiments, the primer incorporating the modified nucleotide is an oligonucleotide designed to form a complex secondary structure consisting of a combination of single-stranded and self-annealed double-stranded regions. In some embodiments, the oligonucleotide is a molecular inversion probe (MIP) (FIG. 2). MIP structures are described in Turner et al., (2009) *Methods for Genomic Partitioning*. Annu. Rev Genomics Hum. Genet., 10:263. MIP is a single-stranded oligonucleotide consisting of two arms complementary to a target sequence separated by a linker sequence non-complementary to the target sequence. The probe-complementary sequences within the target sequence are separated from each other such that the 5'- and 3'-ends of the probe are separated from each other when the probe is hybridized to the target sequence. The gap can be filled by extending the 3'-end of the hybridized probe. Following the strand extension, the two ends can be joined by ligation. Optional exonuclease digestion removes the uncircularized probes.

Figure 3:
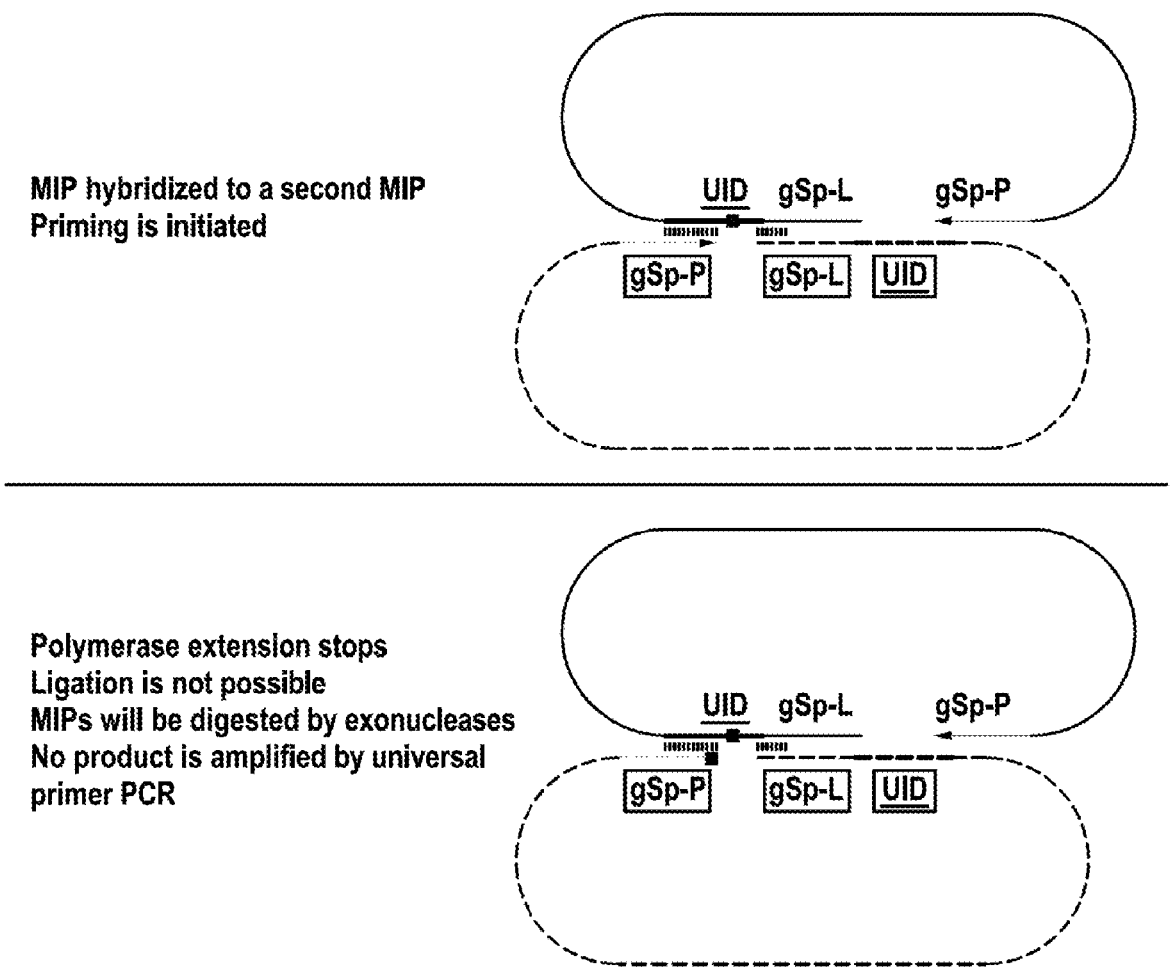
FIG. 3 is a diagram of the method showing a non-extendable artifact formed by molecular inversion probes (MIP).

MIP oligonucleotides may occasionally share regions of complementarity that permit annealing and extension of the 3'-end of the probe to for a complete circle. The circle undergoes ligation and becomes resistant to exonuclease treatment. (FIG. 2). If a modified nucleotide blocking the polymerase is incorporated into the primer, the primer extension and subsequent ligation are prevented. (FIG. 3).

In some embodiments, the method further comprises amplification of the product of the primer extension obtained in the previous steps. The product of the primer extension contains the modified nucleotide in the body of the primer. In the case of a primer with a single region of complementarity (FIG. 1) the method may comprise amplification with gene-specific upstream and downstream primers.

Figure 4:
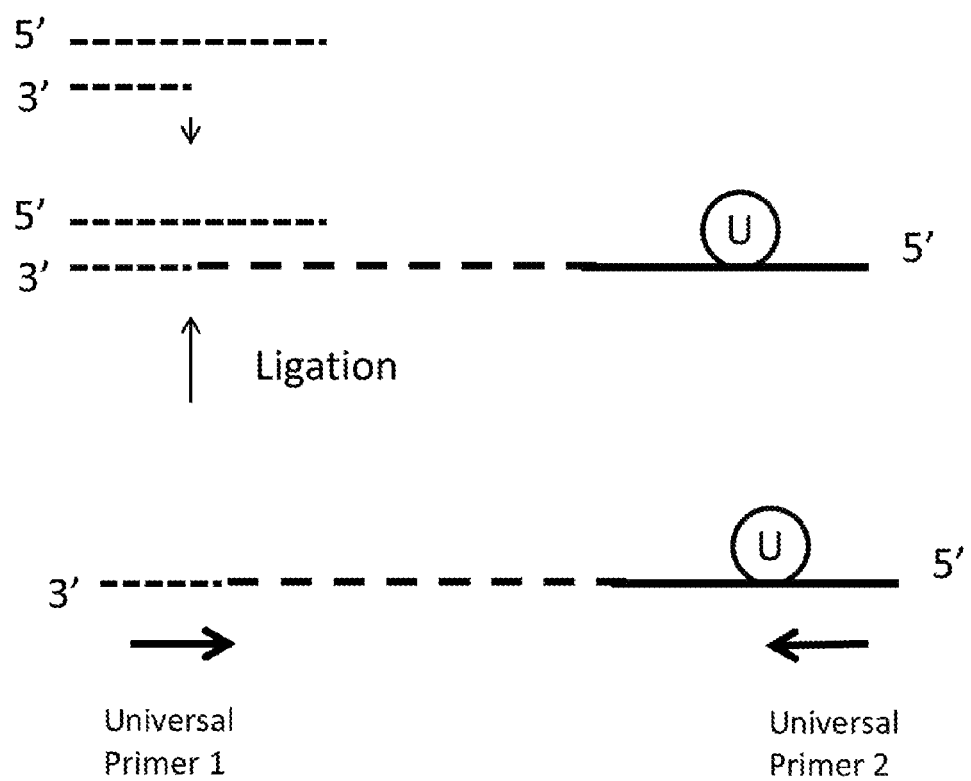
FIG. 4 is a diagram of the method of the invention showing optional amplification steps.
Figure 5:
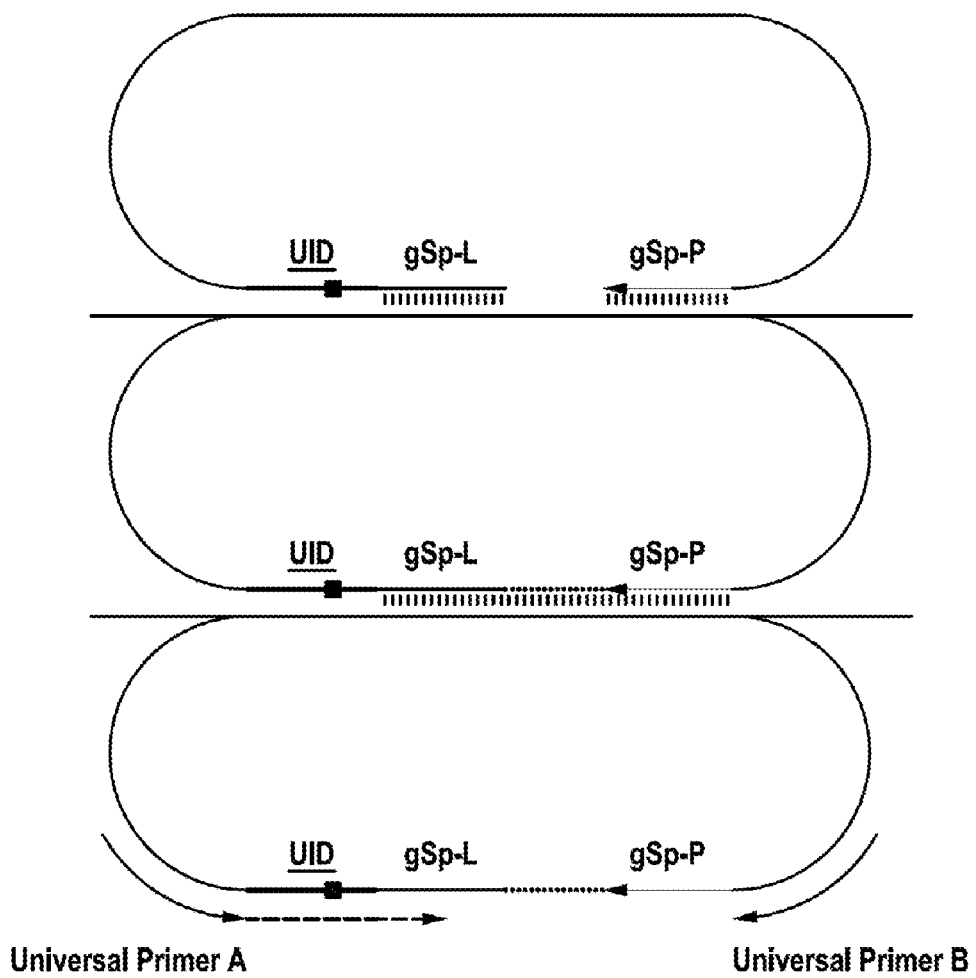
FIG. 5 is a diagram of the method of the invention showing optional amplification steps using molecular inversion probes (MIP).

In other embodiments, universal amplification primers are used. Binding sites for universal primers may be introduced into the initial primer extension primer and into an adaptor ligated to the 3'-terminus of the primer extension product. Ligating adaptors to single-stranded nucleic acids is known in the art, see e.g., U.S. Application Pub. No. 20140193860. Essentially, the method uses a population of adaptors where the single-stranded 3'-end overhang instead of having a universal ligation site, has a random sequence, e.g., a random hexamer sequence. In some embodiments, the initial primer extension primer comprises a binding site for one of the universal primers and the adaptor comprises a binding site for the second universal primer (FIG. 4). In other embodiments, the initial primer extension primer contains binding sites for two universal primers. (FIG. 5).

The amplification may proceed with nucleic acid polymerases tolerant to the presence of the modified nucleotide in the template, i.e., is able to incorporate a base opposite the modified nucleotide and complete the strand synthesis. For example, polymerases able to bypass uracil include thermostable polymerases from thermophilic bacteria, e.g., DNA polymerases from *Thermotoga maritima, Thermus aquaticus, Thermus thermophilus, Thermus flavus, Thermus filiformis, Thermus* species Sps17, *Thermus* species Z05, *Thermus caldophilus, Thermotoga neopolitana*, and *Thermosipho africanus*.

In some embodiments, the method further comprises a step of separating the primer extension products from target nucleic acid template and unused primers. If a uracil-tolerant DNA polymerase is used in the amplification step, the un-extended primer-dimers with uracils must be removed from the reaction mixture.

In the embodiments where the primer incorporating the modified nucleotide is a short oligonucleotide mostly consisting of a single region of partial or exact complementarity with the target nucleic acid (FIG. 1), the primer extension product may undergo ligation and second strand extension. Subsequently, single-stranded nucleic acids including primers can be separated by size.

In the embodiments where the primer incorporating the modified nucleotide is an oligonucleotide designed to form a complex secondary structure consisting of a combination of single-stranded and self-annealed double-stranded regions (e.g., MIP, FIG. 2), the primer extension product is converted into circular DNA without free 3'-OH. In such embodiments unused probes and template DNA can be removed by exonuclease digestion. Single-stranded exonuclease (e.g., Exo I) can be used to remove unused primers and denatured target DNA or sample DNA, and double-stranded exonuclease (e.g., T7 exonuclease) can be used to remove double-stranded target DNA. A mixture of exonucleases can be used to reduce the amount of all nucleic acids in the sample except the ligated (circularized) probes.

In some embodiments, the modified nucleotide is uracil. Incorporation of uracil into the in vitro synthesized DNA can be used for carryover prevention at a facility routinely performing exponential amplification of DNA. Optionally, the uracil-containing DNA contaminant from a prior DNA amplification can be degraded by Uracil DNA Glycosylase (UDG) also known as Uracil-N-DNA Glycosylase (UNG). See Longo, et al., (1990) *Use of uracil DNA glycosylase to control carry-over contamination in polymerase chain reactions*, Gene 93:125. In this embodiment, the UDG treatment is carried out after the primer extension step and prior to the exponential amplification step. The primer extension step is carried over without dUTP in the reaction mixture so that (except for the extension primer), the primer extension product does not incorporate any uracil. In the amplification step, some embodiments would utilize a uracil-tolerant DNA polymerase and dUTP to enable future carryover prevention. In some embodiments, the optional UDG treatment is not carried out. The uracil-containing template does not permit primer extension if the polymerase blocked by uracil is used according to the present invention. The single-stranded carryover nucleic acid with a non-extended primer is digested with nucleases.

The methods of the instant invention can be used as a part of a more complex experimental design. In some embodiments, the products of the primer extension or subsequent amplification are used for nucleic acid sequencing protocol, including high throughput single molecule sequencing. Specifically, the method can be a part of a library generation step wherein the multiplex primer extension (and optional amplification) generates a library of target nucleic acids to be sequenced. The target nucleic acids in the library may be modified to incorporate barcodes for molecular identification (unique molecular ID (MID)) and sample identification (multiplex sample ID (SID)). These barcode sequences may incorporated one or both primers or into the adaptor.

Sequencing can be performed by any method known in the art. Especially advantageous is the high-throughput single molecule sequencing. Examples of such technologies include Illumina HiSeq platform (Illumina, San Diego, Cal.), Ion Torrent platform (Life Technologies, Grand Island, NY), Pacific BioSciences platform utilizing the SMRT" reagents (Pacific Biosciences, Menlo Park, Cal.), or nanopore-based sequencing technology developed by Genia Technologies (Mountain View, Cal.) or Oxford Nanopore Technologies (Cambridge, UK) or any other presently existing or future single-molecule sequencing technology that does or does not involve sequencing by synthesis. In some embodiments, the sequencing utilizes a universal primer site present in adaptors ligated to one or both ends of the target nucleic acid or in primers used to copy of amplify the target nucleic acids prior to sequencing. In yet other embodiments, a gene-specific primer is used for sequencing.

A sample used in the method of the invention comprises any sample from an individual (e.g., human patient) or environmental sample or a laboratory preparation containing nucleic acids. The polynucleotides can be extracted from the sample, or the sample can be directly subjected to the methods of the invention. The starting sample can also be extracted or isolated nucleic acids, DNA or RNA. The sample can constitute any tissue or fluid obtained from an organism. For example, the sample may be a tumor biopsy or a blood or plasma sample. In some embodiments, the sample is a formalin-fixed, paraffin-embedded (FFPE) sample. The sample may comprise nucleic acids from one or more sources, e.g., one or more patients. In some embodiments, the tissues can be infected with a pathogen and thus contain host's and pathogen's nucleic acids.

Methods of DNA extraction are well-known in the art. See J. Sambrook et al., "Molecular Cloning: A Laboratory Manual," 1989, 2nd Ed., Cold Spring Harbor Laboratory Press: New York, N.Y.). A variety of kits are commercially available for extracting nucleic acids (DNA or RNA) from biological samples (e.g., BD Biosciences Clontech (Palo Alto, Cal.), Epicentre Technologies (Madison, Wisc.); Gentra Systems, Inc. (Minneapolis, Minn.); and Qiagen, Inc. (Valencia, Cal.), Ambion, Inc. (Austin, Tex.); BioRad Laboratories (Hercules, Cal.); and more.

In some embodiments, the starting sample used in the method of the invention is a library, e.g., a genomic library or an expression library that comprises a plurality of polynucleotides. In other embodiments, a library is created using the primer extension method of the invention. With the starting material being a biological sample, the method creates an amplification library, or a collection of amplicons representing variety or sequences. A library can be stored and used multiple times for further amplification or sequencing of the nucleic acids in the library.

In some embodiments, the invention is a kit for primer extension of a target nucleic acid that avoids or has a reduced number of primer dimers. The kit comprises one or more target-specific primers containing a modified base and a nucleic acid polymerase that stalls strand synthesis upon reaching the modified base in the template strand. In some embodiments, the polymerase is an archaeal polymerase. In some embodiments, the modified base is uracil and the polymerase is an archaeal B-family polymerase. In other embodiments, the modified nucleotide is abasic and the polymerase is a replicative polymerase. In yet other embodiments, the modified nucleotide is a pyrimidine dimer and the polymerase is a replicative polymerase. In some embodiments, the kit further comprises an adaptor. The adaptor may comprise sequences necessary for further in vitro analysis steps, such as one or more molecular barcodes, ligation sites and universal primer binding sites. The kit may also reagents and enzymes for nucleic acid synthesis, amplification, ligation and purification including exonuclease digestion of excess primers and probes.

In some embodiments, the invention is a reaction mixture for primer extension of a target nucleic acid that avoids or has a reduced number of primer dimers. The reaction mixture comprises one or more target-specific primers containing a modified base and a nucleic acid polymerase that stalls strand synthesis upon reaching the modified base in the template strand. In some embodiments, the polymerase is an archaeal polymerase. In some embodiments, the modified base is uracil and the polymerase is an archaeal B-family polymerase. In other embodiments, the modified nucleotide is abasic and the polymerase is a replicative polymerase. In yet other embodiments, the modified nucleotide is a pyrimidine dimer and the polymerase is a replicative polymerase.

EXAMPLES

Example 1 (Prophetic) Target Capture with Reduced Cross-Reactivity of Molecular Inversion Probes (MIP)

Molecular inversion probes (MIP) have been used to enrich for target sequences in next generation sequencing applications. The probe pools used can generate hundreds and even thousands of target amplicons. However, designing probes to perform well in the context of hundreds or thousands of other probes is not trivial. This is due to interactions that can occur between probes creating undesirable products in final libraries. This situation can be exacerbated when using unique identifier sequences in these probes as they are random sequences engineered into the probes to enable molecule identification via sequencing. Incorporating uracil bases into the molecular inversion probes should reduce the generation of undesirable products by blocking polymerase extension when two probes interact.

As shown in FIG. 2, if one MIP hybridizes to another MIP, primer extension is initiated, ligation closes the circle and the resulting product is protected from nuclease digestion. According to the invention, the MIP containing uracil is incubated with the target nucleic acid and the polymerase according to the standard reaction conditions recommend for MIP. The reaction mixture is subjected to primer extension, ligation and optionally, subsequent amplification. There is an optional step of digesting the linear (non-circular) nucleic acids with exonuclease. A mixture of single-stranded and double-stranded exonucleases (ExoI and T7 exonuclease) is used. As shown in FIG. 3, the primer-primer interaction may result in hybridization, but there is no primer extension and no ligation in the hybridization product. During the amplification step, the hybridization product cannot be amplified. The subsequent amplification is carried out with a uracil-tolerant polymerase. If carryover prevention is desired, after the primer extension step, the reaction mixture is treated with UDG. If subsequent carryover prevention is desired, the amplification is carried out in the presence of dUTP.

The invention claimed is:

1. A method of amplifying a target nucleic acid in a sample with reduced primer-primer interaction comprising:
   (a) a primer extension step, wherein the sample is contacted with: (i) a nucleic acid polymerase, and (ii) a first primer which is a single-stranded oligonucleotide comprising at least one modified nucleotide that stalls nucleotide incorporation by the polymerase, the first primer comprising two arms complementary to a target sequence separated by a linker sequence non-complementary to the target sequence, such that a gap is created between the ends of the two arms when the first primer hybridizes to the target nucleic acid, wherein the polymerase fills the gap between the ends of the two arms; and
   (b) an exponential amplification step wherein the sample is contacted with a second primer complementary to the primer extension product and a polymerase tolerant of the modified nucleotide.

2. The method of claim 1, wherein the first primer comprises binding sites for universal amplification primers and the second primer is a universal primer.

3. The method of claim 1, wherein the modified nucleotide is uracil.

4. A reaction mixture for synthesizing nucleic acid strands according to claim 1, comprising a target nucleic acid, a nucleic acid polymerase and a first primer which is a single-stranded oligonucleotide consisting of two arms complementary to a target sequence separated by a linker sequence non-complementary to the target sequence and comprising at least one modified nucleotide that stalls nucleotide incorporation by the polymerase.

5. The method of claim 1, further comprising a step of joining the ends of the extended first primer by ligation.

6. The method of claim 5, further comprising prior to step (b), contacting the sample with an endonuclease.

7. The method of claim 1, wherein the first primer comprises a unique molecular barcode.

8. The method of claim 1, wherein the second primer comprises a sample barcode.

9. The method of claim 1, further comprising sequencing the amplified nucleic acid from step (b).

10. The method of claim 9, wherein a universal sequencing primer site is located in the second primer.

* * * * *